US010772742B2

(12) United States Patent
Lenzi et al.

(10) Patent No.: US 10,772,742 B2
(45) Date of Patent: Sep. 15, 2020

(54) POLYCENTRIC POWERED ANKLE PROSTHESIS

(71) Applicant: REHABILITATION INSTITUTE OF CHICAGO, Chicago, IL (US)

(72) Inventors: Tommaso Lenzi, Chicago, IL (US);
Marco Cempini, Chicago, IL (US);
Todd Kuiken, Chicago, IL (US)

(73) Assignee: Rehabilitation Institute of Chicago, Chicago, IL (US)

( * ) Notice: Subject to any disclaimer, the term of this patent is extended or adjusted under 35 U.S.C. 154(b) by 0 days.

(21) Appl. No.: 15/482,663

(22) Filed: Apr. 7, 2017

(65) Prior Publication Data

US 2017/0290684 A1    Oct. 12, 2017

Related U.S. Application Data

(60) Provisional application No. 62/319,430, filed on Apr. 7, 2016.

(51) Int. Cl.
| | | |
|---|---|---|
| A61F 2/66 | (2006.01) |
| A61F 2/70 | (2006.01) |
| A61F 2/50 | (2006.01) |
| A61F 2/68 | (2006.01) |
| A61F 2/76 | (2006.01) |

(52) U.S. Cl.
CPC ............... *A61F 2/6607* (2013.01); *A61F 2/70* (2013.01); *A61F 2002/5018* (2013.01); *A61F 2002/5021* (2013.01); *A61F 2002/5027* (2013.01); *A61F 2002/5038* (2013.01); *A61F 2002/6614* (2013.01); *A61F 2002/6836* (2013.01); *A61F 2002/701* (2013.01); *A61F 2002/7635* (2013.01)

(58) Field of Classification Search
CPC .................................................. A61F 2/6607
See application file for complete search history.

(56) References Cited

U.S. PATENT DOCUMENTS

| | | | |
|---|---|---|---|
| 3,874,004 A * | 4/1975 | May .......................... A61F 2/66 |
| | | | 623/50 |
| 5,181,931 A | 1/1993 | van de Veen | |
| 5,759,168 A | 6/1998 | Bussell et al. | |
| 6,443,994 B1 | 9/2002 | Kubein-Meesenburg et al. | |
| 2009/0171469 A1 | 7/2009 | Thorsteinsson et al. | |

(Continued)

FOREIGN PATENT DOCUMENTS

| | | |
|---|---|---|
| DE | 3907195 A1 | 9/1989 |
| GB | 2283920 | 5/1995 |
| WO | 01/49221 | 7/2001 |

OTHER PUBLICATIONS

S. Hamner, V. Narayan, K. Donaldson, "for Scale: Development of the ReMotion Knee for Global Emerging Markets", Annals of Biomedical Engineering vol. 41, No. 9, Sep. 2013, pp. 1851-1859.

(Continued)

*Primary Examiner* — David H Willse
(74) *Attorney, Agent, or Firm* — McAndrews, Held & Malloy, Ltd.

(57) ABSTRACT

Systems and methods are disclosed for a powered ankle prosthesis. The prosthesis may comprise a polycentric mechanism having a defined path for an instantaneous center of rotation. The path of the instantaneous center of rotation may be defined by a trajectory substantially equal to an arc positioned over a joint of the polycentric mechanism.

15 Claims, 13 Drawing Sheets

(56) References Cited

U.S. PATENT DOCUMENTS

| | | | |
|---|---|---|---|
| 2014/0039642 A1* | 2/2014 | Nijiman | A61F 2/6607 623/33 |
| 2014/0243997 A1* | 8/2014 | Clausen | A61F 2/66 623/55 |
| 2015/0209214 A1 | 7/2015 | Herr et al. | |
| 2015/0359643 A1 | 12/2015 | Terleski et al. | |

OTHER PUBLICATIONS

Grabowski and D'Andrea, "Effects of a powered ankle-foot prosthesis on kinetic loading of the unaffected leg during level-ground walking", Journal of NeuroEngineering and Rehabilitation 2013, 10:49 pp. 1-11.

S. Au, M. Berniker, H. Herr, "Powered ankle-foot prosthesis to assist level-ground and stair-descent gaits," Neural Networks, 2008, pp. 654-666, 21.

J. Geeroms, L. Flynn, R. Jimenez-Fabian, B. Vanderborght, D. Lefeber, "Ankle-Knee Prosthesis with Powered Ankle and Energy Transfer for CYBERLEGs α-Prototype," 2013 IEEE International Conference on Rehabilitation Robotics, 2013, (6 pages).

L. Flynn, J. Geeromsa, R. Jimenez-Fabian, B. Vanderborght, N. Vitiello, D. Lefeber, "Ankle—knee prosthesis with active ankle and energy transfer: Development of the CYBERLEGs Alpha-Prosthesis," Robotics and Autonomous Systems, 2015, pp. 4-15, 73.

J. Hitt, T. Sugar, M. Holgate, R. Bellman, K. Hollander, "Robotic transtibial prosthesis with biomechanical energy regeneration," Industrial Robot: An International Journal, 2009, pp. 441-447, 36/5.

R. Jiménez-Fabián, O. Verlinden, "Review of control algorithms for robotic ankle systems in lower-limb orthoses, prostheses, and exoskeletons," Medical Engineering & Physics, 2012, pp. 397-408, 34.

R. Versluys, P. Beyl, M. Van Damme, A. Desomer, R. Van Ham, D. Lefeber, "Prosthetic feet: State-of-the-art review and the importance of mimicking human ankle—foot biomechanics," Disability and Rehabilitation: Assistive Technology, 2009, pp. 65-75, 4/2.

A. Huff Shultz, J. E. Mitchell, D. Truex, B. E. Lawson, M. Goldfarb, "Preliminary Evaluation of a Walking Controller for a Powered Ankle Prosthesis," 2013 IEEE International Conference on Robotics and Automation (ICRA), 2013, pp. 4838-4842.

F. Sup, A. Bohara, M. Goldfarb, "Design and Control of a Powered Transfemoral Prosthesis," The International Journal of Robotics Research, 2008, pp. 263-273, 27/2.

A. H. Shultz, B. E. Lawson, M. Goldfarb, "Running With a Powered Knee and Ankle Prosthesis," IEEE Transactions on Neural Systems and Rehabilitation Engineering, 2015, pp. 403-412, 23/3.

Ossur, "Instructions for Use, PRO-FLEX, Product No. PFP0xyyz," Manual, 2016, pp. 1-77.

P. F. Adams, G. E. Hendershot, and M. A. Marano, "Current estimates from the National Health Interview Survey, 1996.," Natl. Heal. Surv. Vital Heal. Stat., 1999, pp. 1-203, No. 200.

K. Ziegler-Graham, E. J. Mackenzie, P. L. Ephraim, T. G. Travison, and R. Brookmeyer, "Estimating the Prevalence of Limb Loss in the United States: 2005 to 2050," Arch. Phys. Med. Rehabil., 2008, pp. 422-429, vol. 89, No. 3.

T. Schmalz, S. Blumentritt, and R. Jarasch, "Energy expenditure and biomechanical characteristics of lower limb amputee gait: The influence of prosthetic alignment and different prosthetic components," Gait Posture, 2002, pp. 255-263, vol. 16, No. 3.

E. H. Sinitski, A. H. Hansen, and J. M. Wilken, "Biomechanics of the ankle-foot system during stair ambulation: Implications for design of advanced ankle-foot prostheses," J. Biomech., 2012, pp. 588-594, vol. 45.

S. H. Collins and A. D. Kuo, "Recycling energy to restore impaired ankle function during human walking.," PLoS One, 2010, pp. e9307, vol. 5, No. 2.

E. Nickel, J. Sensinger, and A. Hansen, "Passive prosthetic ankle-foot mechanism for automatic adaptation to sloped surfaces," J. Rehabil. Res. Dev., 2014, pp. 803-814, vol. 51, No. 5.

L. Fradet, M. Alimusaj, F. Braatz, and S. I. Wolf, "Biomechanical analysis of ramp ambulation of transtibial amputees with an adaptive ankle foot system," Gait Posture, 2010, pp. 191-198, vol. 32, No. 2.

Https://www.ossur.com/prosthetic-solutions/products/dynamicsolutions/proprio-foot, "Ossur Proprio Foot." (5 pages.), downloaded on Feb. 7, 2018.

S. Au and H. Herr, "Powered ankle-foot prosthesis," IEEE Robot. Autom. Mag., 2008, pp. 52-59, vol. 15, No. 3.

A. H. Shultz, J. E. Mitchell, D. Truex, B. E. Lawson, and M. Goldfarb, "Preliminary evaluation of a walking controller for a powered ankle prosthesis," 2013 IEEE Int. Conf. Robot. Autom., 2013, pp. 4838-4843.

M. Goldfarb, B. E. Lawson, and A. H. Shultz, "Realizing the promise of robotic leg prostheses.," Sci. Transl. Med., 2013, p. 210ps15, vol. 5, No. 210.

BionX, "emPOWER Ankle Instructions for Use." 2016. (32 pages).

A. E. Ferris, J. M. Aldridge, C. A. Rábago, and J. M. Wilken, "Evaluation of a Powered Ankle-Foot Prosthetic System During Walking," Arch. Phys. Med. Rehabil., 2012, pp. 1911-1918, vol. 93, No. 11.

J. D. Smith and P. E. Martin, "Effects of Prosthetic Mass Distribution on Metabolic Costs and Walking Symmetry.," J. Appl. Biomech., Sep. 2012.

G. Klute, J. Czerniecki, B. Hannaford, "McKibben Artificial Muscles: Pneumatic Actuators with Biomechanical Intelligence", IEEE/ASME 1999 Int'l Conf. on Adv. Intelligent Mechatronics, Sep. 19-22, 1999, pp. 1-6.

D. Villegas, M. Van Damme, B. Vanderborght, P. Beyl, and D. Lefeber, "Third-Generation Pleated Pneumatic Artificial Muscles for Robotic Applications: Development and Comparison with McKibben Muscle," Adv. Robot., Jul. 2012, pp. 1205-1227, vol. 26, No. 11-12.

M. A. Holgate, J. K. Hitt, R. D. Bellman, T. G. Sugar, and K. W. Hollander, "The SPARKy (Spring Ankle with Regenerative kinetics) project: Choosing a DC motor based actuation method," in 2008 2nd IEEE RAS & EMBS International Conference on Biomedical Robotics and Biomechatronics, 2008, pp. 163-168.

P. Cherelle, V. Grosu, A. Matthys, B. Vanderborght, and D. Lefeber, "Design and Validation of the Ankle Mimicking Prosthetic (AMP-) Foot 2.0.," IEEE Trans. Neural Syst. Rehabil. Eng., Oct. 2013., pp. 138-148, vol. 22, No. 1.

J. K. Hitt, T. G. Sugar, M. Holgate, and R. Bellman, "An Active Foot-Ankle Prosthesis With Biomechanical Energy Regeneration," Journal of Medical Devices, 2010, p. 11003, vol. 4, No. 1.

L. Flynn, J. Geeroms, R. Jimenez-Fabian, B. Vanderborght, N. Vitiello, and D. Lefeber, "Ankle-knee prosthesis with active ankle and energy transfer: Development of the CYBERLEGs Alpha-Prosthesis," in Robotics and Autonomous Systems, 2015, vol. 73, pp. 4-15.

B. Lawson, J. Mitchell, D. Truex, A. Shultz, E. Ledoux, and M. Goldfarb, "A Robotic Leg Prosthesis: Design, Control, and Implementation.," Robot. Autom. Mag., 2014, pp. 70-81, vol. 21, No. 4.

A. H. Shultz, B. E. Lawson, and M. Goldfarb, "Variable Cadence Walking and Ground Adaptive Standing With a Powered Ankle Prosthesis," IEEE Trans. Neural Syst. Rehabil. Eng., Apr. 2016, pp. 495-505, vol. 24, No. 4.

M. Grimmer, M. Holgate, R. Holgate, A. Boehler, J. Ward, K. Hollander, T. Sugar, and A Seyfarth, "A powered prosthetic ankle joint for walking and running," Biomed. Eng. Online, Dec. 2016, p. 286, vol. 15.

J. D. Smith and P. E. Martin, "Short and Longer Term Changes in Amputee Walking Patterns Due to Increased Prosthesis Inertia," JPO J. Prosthetics Orthot., Jul. 2011., pp. 114-123, vol. 23, No. 3.

Y. Narang, V. Arelekatti, and A. Winter, "The Effects of Prosthesis Inertial Properties on Prosthetic Knee Moment and Hip Energetics Required to Achieve Able-bodied Kinematics," IEEE Trans. Neural Syst. Rehabil. Eng., pp. 754-763, Jul. 2016, vol. 24 No. 7.

J. M. Caputo and S. H. Collins, "A Universal Ankle-Foot Prosthesis Emulator for Human Locomotion Experiments," J. Biomech. Eng., 2014, p. 35002, vol. 136, No. 3.

(56) References Cited

OTHER PUBLICATIONS

S. Hamner, V. Narayan, N. Rappin, and K. Donaldson, "ReMotion Knee: Scaling of an Affordable Prosthetic Knee for Developing Countries," in Technologies for Development, 2015, pp. 137-151.
M. P. Aragon, G. A. V. Orozco, and A. A. Altamirano, "Bionic hip prosthesis based on polycentric mechanisms," in 2013 Pan American Health Care Exchanges (PAHCE), 2013, pp. 1-5.
L. Xu, D.-H. Wang, Q. Fu, G. Yuan, and L.-Z. Hu, "A novel four-bar linkage prosthetic knee based on magnetorheological effect: principle, structure, simulation and control," Smart Mater. Struct., Nov. 2016, p. 115007, vol. 25, No. 11.
S. Pfeifer, R. Riener, and H. Vallery, "An actuated transfemoral prosthesis with optimized polycentric knee joint," Proc. IEEE RAS EMBS Int. Conf. Biomed. Robot. Biomechatronics, 2012, pp. 1807-1812.
A. Laprè and F. Sup, "A Control Strategy for an Active Alignment Transtibial Prosthesis," in ASME Dynamic Systems and Control Conference, 2015, p. V001T18A005.
G. Bovi, M. Rabuffetti, P. Mazzoleni, and M. Ferrarin, "A multiple-task gait analysis approach: kinematic, kinetic and EMG reference data for healthy young and adult subjects.," Gait Posture, Jan. 2011, pp. 6-13, vol. 33, No. 1.
D. A. Winter, Biomechanics and Motor Control of Human Movement, University of Waterloo. 1990, vol. 2. Wiley. (286 pages).
T. Lenzi, L. Hargrove, and J. W. Sensinger, "Preliminary evaluation of a new control approach to achieve speed adaptation in robotic transfemoral prostheses," in IEEE/RSJ International Conference on Intelligent Robots and System, 2014, 2014.
T. Lenzi, L. Hargrove, and J. Sensinger, "Speed-adaptation mechanism: Robotic prostheses can actively regulate joint torque," IEEE Robot. Autom. Mag., 2014, pp. 94-107, vol. 21, No. 4.
Andrew Lapre, Frank Sup, "A control strategy for an active alignment transtibial prosthesis," ASME 2015 Dynamic Systems and Control Conference, 2015, pp. V001T18A005, vol. 1.
Int'l Search Report and Written Opinion Appln No. PCT/US2017/26703 dated Dec. 29, 2017 (11 pages).
Alberto Leardini et al. "Biomechanics of the Natural, Arthritic, and Replaced Human Ankle Joint," Journal of Foot and Ankle Research, published on Feb. 2014 (Feb. 2014), A retrieved on Nov. 22, 2017 (Nov. 22, 2017), accessed at <https://www.researchgate.net/publication/260116283_Biomechanics_of_the_natural_arthritic_and_replaced_human_anklejoint>, entire document, especially Fig. 2; p. 2, col. 2, para 2-3.
H. Herr, A. Grabowski, "Bionic ankle-foot prosthesis normalizes walking gait for persons with leg amputation", Proceedings: Biological Sciences, vol. 279, No. 1728 (Feb. 7, 2012) pp. 457-464.
M. Cempini, L. Hargrove, T. Lenzi, "Design, Development, and Bench-top Testing of a Powered Polycentric Ankle Prosthesis" IEEE/RSJ Int'l Conf. on Intelligent Robots and Systems 2017 (7 pages).

* cited by examiner

POLYCENTRIC POWERED ANKLE PROSTHESIS

RELATED APPLICATIONS

This patent claims priority to U.S. Provisional Patent Application Ser. No. 62/319,430, filed on Apr. 7, 2016, entitled "Polycentric Powered Ankle Prosthesis." The entirety of U.S. Provisional Patent Application Ser. No. 62/319,430 is incorporated herein by reference.

CROSS REFERENCE TO RELATED APPLICATION

This application is a non-provisional that claims benefit to U.S. Provisional Patent Application No. 62/319,430 filed on Apr. 7, 2016, which is herein incorporated by reference in its entirety.

FEDERALLY SPONSORED RESEARCH OR DEVELOPMENT

This invention was made with government support under Award No. 90RE5014-02-00 awarded by the National Institute on Disability, Independent Living, and Rehabilitation Research (NIDILRR), an agency of the United States Department of Health and Human Services, and under Award No. W81XWH-14-C-0105 awarded by the United States Army. The government has certain rights in the invention.

BACKGROUND

Prosthetic ankle devices are frequently used as replacement after the loss of lower limb following amputation. Prostheses can fulfill both the aesthetic and the functional role of the lower leg, such as running, sports, or other exercise; climbing or descending stairs; ascending or descending slopes; level walking; other movement; and restoration of the appearance of the missing limb.

A sound human ankle helps a person walk during gait. The phase of gait where the foot touches the ground is known as the stance phase of gait. In the initial part of stance phase (from heel-strike to mid-stance), the ankle stores elastic energy in the elongation of its tendons. In late-stance (from mid-stance to toe-off), the energy stored in the tendons is returned, along with the addition of an active muscle-powered component. This energy propels a person forward while walking. Such behavior cannot be replicated by passive or quasi-passive prosthesis that require the user to supply this missing energy, such as by pushing forward the user's body center of mass on toe-off; through an increased torque in the remaining lower-limb joints (mainly the hip); or by altering the symmetry of the gait between the two limbs.

Some prostheses are fully powered. Powered ankle prostheses have the potential to provide substantial benefits for amputees and provide further opportunities for clinical research. However, powered ankle prostheses known in the art have drawbacks in technology and implementation. Achieving one or more of the design goals of appropriate battery duration, structural strength, high range of motion and lightness are difficult to meet while also enclosing the design of the ankle prosthesis into an anatomical shape, such as a shape that would fit within the user's shoe. Moreover, interchangeability and modularity (such as interfacing with the stump's socket, or pylon or torsion-elements) can be a problem due to the prosthesis dimensions and built-height, especially for transtibial amputees.

BRIEF SUMMARY

In various embodiments, a powered ankle prosthesis is disclosed. The prosthesis may comprise a polycentric mechanism having a defined path for an instantaneous center of rotation; wherein the path of the instantaneous center of rotation is defined by a trajectory substantially equal to an arc positioned over a joint of the polycentric mechanism. The path of the instantaneous center of rotation may be further defined such that during late stance, the instantaneous center of rotation is positioned to provide a shortened moment arm in relation to a ground reaction force.

The polycentric mechanism may comprise a first member and a second member. The first member may define the path for the instantaneous center of rotation. The first member may comprise a base element connected to a foot component, a first crank pivotally coupled to the first member, and a second crank pivotally coupled to the first member. The first crank and the second crank each may be pivotally coupled to a bottom portion of the second member. The first crank and the second crank each may be aligned to define the path for the instantaneous center of rotation. A top portion of the second member may be angled for attachment to a shank component connection.

In various embodiments, the prosthesis may further comprise an actuator for moving the polycentric mechanism. The actuator may be at least partially housed within an opening of the polycentric mechanism. The actuator may be configured to adjust the distance between a hinge of the first member and a hinge of the driven member. The actuator may comprise a motor, a transmission, and a screw. The screw may be, for example, a leadscrew, a ballscrew, or a rollerscrew.

The polycentric mechanism of the prosthesis may fit within the contour of an anatomical foot profile.

BRIEF DESCRIPTION OF THE DRAWINGS

Reference is further made to the following description taken with the accompanying drawings.

DETAILED DESCRIPTION

Figure 1A:
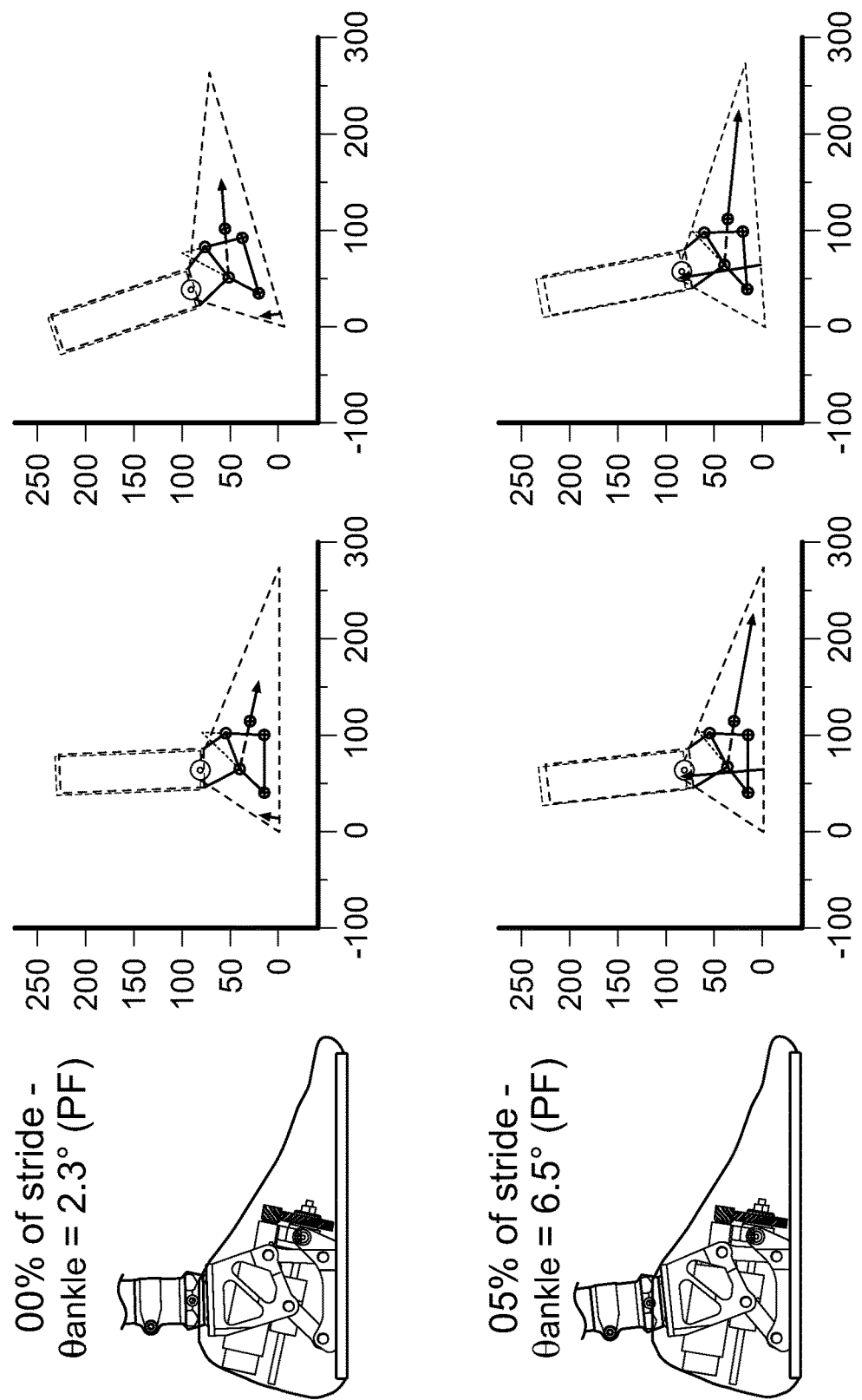
FIGS. 1A-1D display side views of an embodiment of an ankle prosthesis at positions ranging from 0% of stride to 60% of stride, and kinematic diagrams corresponding to each position.
Figure 1B:
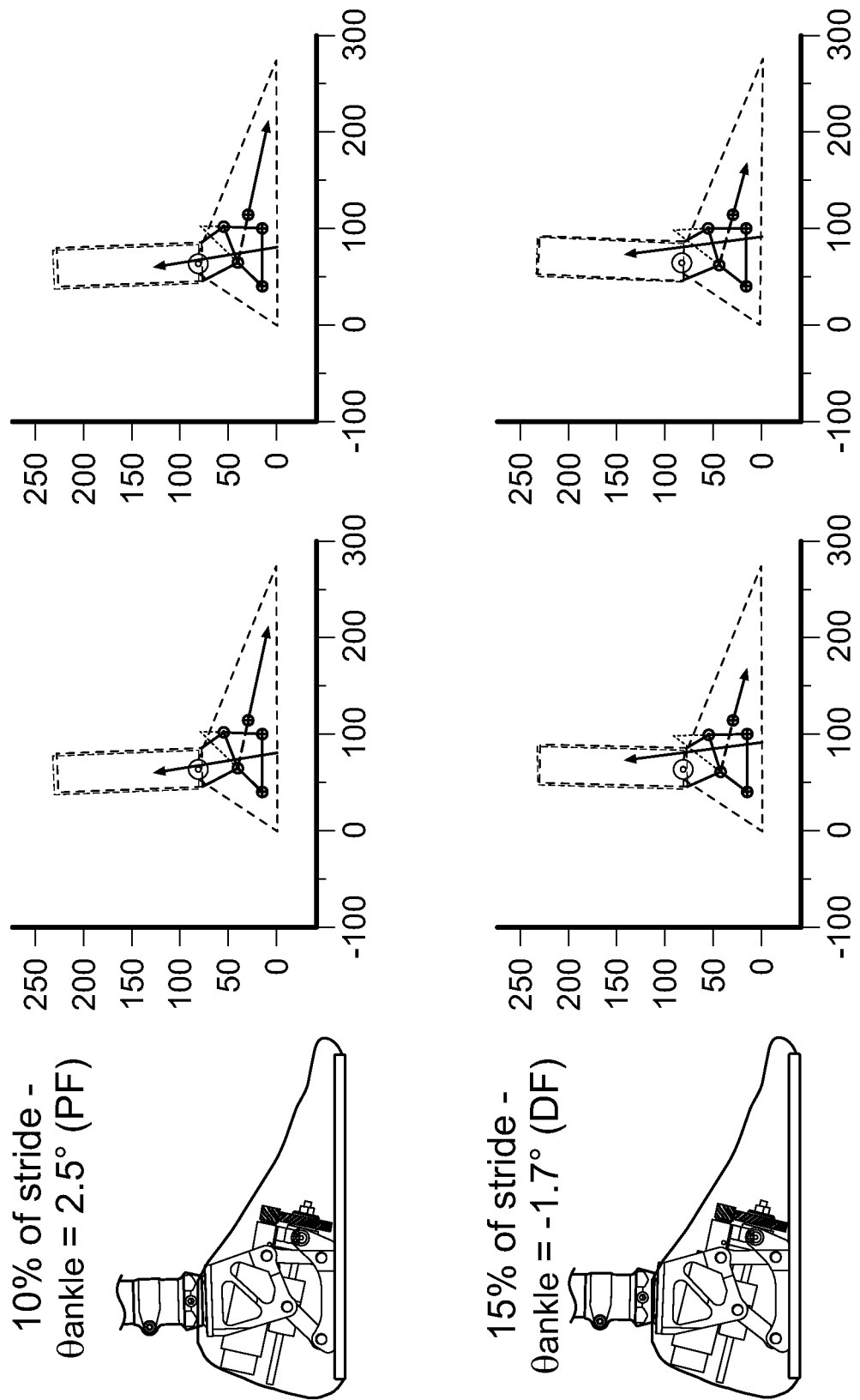
Figure 1B:
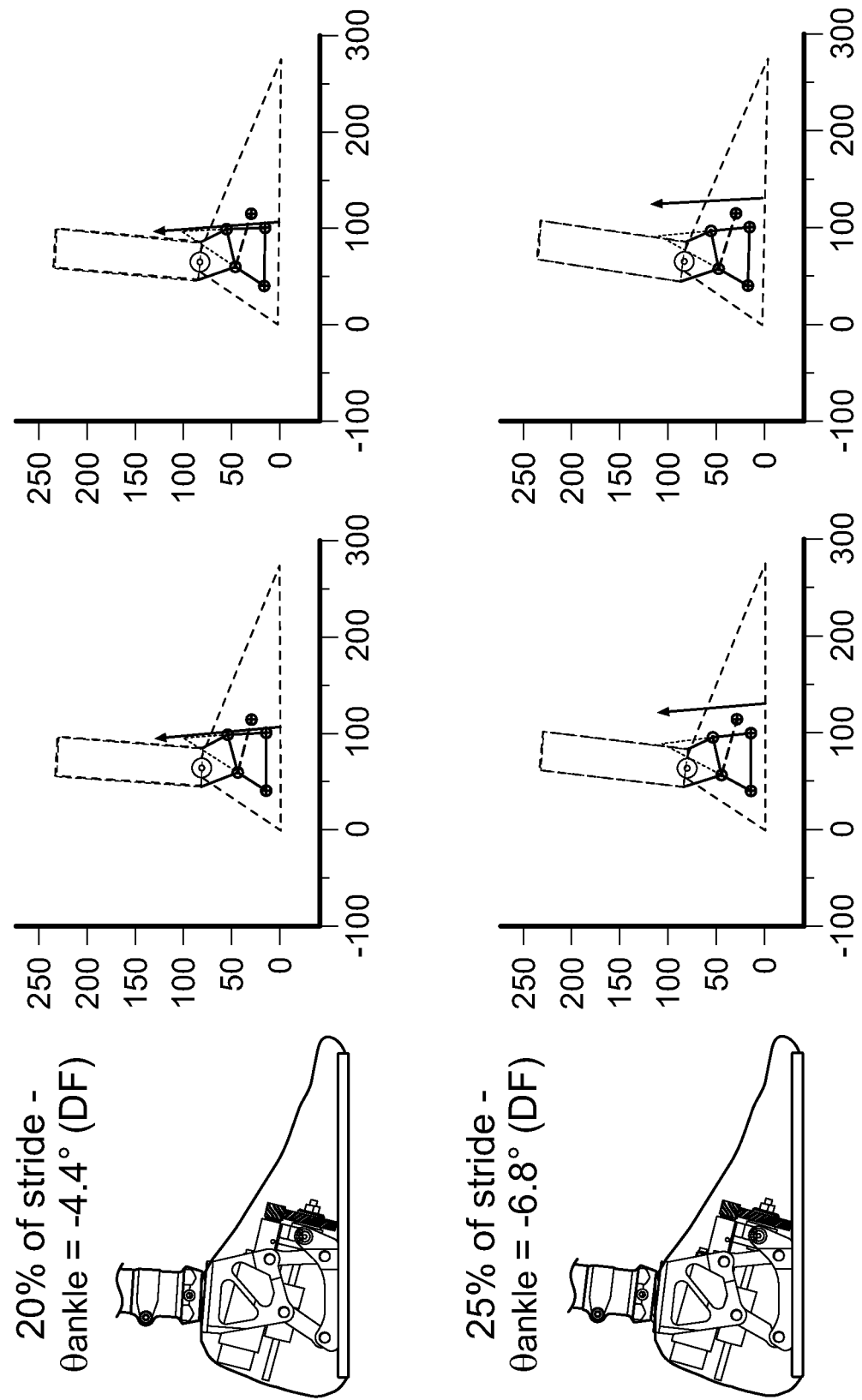

In certain embodiments, a powered ankle prosthesis is disclosed that employs a polycentric mechanism. A polycentric mechanism is one where the center of rotation of at least a portion of the mechanism changes in response to the position of at least a portion of the mechanism. The center of rotation of a polycentric mechanism is known as an "instantaneous center of rotation" or "ICR". It is referred to as "instantaneous" because it is the center of rotation of at least a portion of the polycentric mechanism, at the particular instant at which the mechanism is at a particular position.

In an embodiment, a polycentric mechanism may comprise a first member and a second member. The first member and the second member may be connected by a joint structure. For example, the joint structure may comprise a plurality of joints that connect the first member and the second member.

Each member may comprise a one or more members to form a linkage. The polycentric mechanism may preserve one "degree of freedom," meaning that only one parameter is needed to describe the posture of the polycentric mechanism. The motion of the polycentric mechanism may be shared among multiple joints within the mechanism which move simultaneously. The resultant motion may be a combination of both translational and rotational motion. The nature of this motion can be characterized by the position of the instantaneous center of rotation as the polycentric mechanism moves from one position to another. For example, the polycentric mechanism may be integrated into a powered ankle-foot prosthesis that can be worn by a person, and which helps the person walk. When the person begins the gait phase of stance, he or she brings the heel of the prosthesis to the ground ("heel strike"). When the person ends the gait phase of stance, he or she lifts the toe of the prosthesis from the ground ("toe off"). The nature of the motion of the polycentric mechanism can be characterized by the position of the instantaneous center of rotation as the polycentric mechanism moves from the heel strike position to the toe off position.

Using a polycentric mechanism can provide certain benefits to a battery powered foot-ankle prosthesis, such as a powered foot-ankle prosthesis that employs a battery-powered actuator to move, or actuate, the polycentric mechanism. For example, using a polycentric mechanism allows for the instantaneous center of rotation to extend outside of the profile of the polycentric mechanism, as shown, for example, in certain of the figures herein. As a result, the amount of torque the actuator must produce to provide in certain phases of gait (such as late stance, when the ankle needs to provide more torque in order to push off from the ground) may be reduced. This allows for a prosthesis that employs a smaller actuator, a smaller battery, and/or an actuator that can operate for a longer period of time before the battery runs out of energy.

In one embodiment, the polycentric mechanism may comprise a four-bar linkage, where two members of the linkage are connected by two distinct cranks, hinged to both members: the relative motion between the members is a rotation around the ICR, which can be detected by the intersection of the direction of the two cranks.

There are several features for a powered ankle prosthesis which can be optimized through a proper sizing of actuated four-bar linkages. For example, the ICR progression may be optimized so as to minimize the work-load for a motor that provides power to the prosthesis. As another example, the range of motion of the prosthesis may be adjusted to be comparable with the natural range of motion of a human ankle. As yet another example, the translational portion of motion may be optimized as to be less evident, for an intended use of the prosthesis.

Another feature of certain embodiments described herein is a translational movement of the ankle prosthesis, instead of angular movement, with respect to the residual limb, as to minimize the shear stresses transmitted through the cuff to the residual leg stump.

Another feature of certain embodiments described herein is that the actuator may be enclosed within an opening in the polycentric mechanism. Another feature of certain embodiments is that the structural strength of the ankle-foot prosthesis is shared among more connecting members that carry both the user's weight and the powered loads, which can reduce the overall weight of the prosthesis.

In certain embodiments, a powered ankle prosthesis may comprise a polycentric mechanism that provides a swiveling motion between a first member and a second member. The first member may be referred to as the "reference" member and second member may be referred to as the "driven" member. The swiveling motion between the reference member and the driven member can result in the driven member rotating with respect to the reference member. Either member may be linked to a foot prosthetic component, or element, and the other member may be linked to a shank prosthetic component, or element. The foot component and the shank component may be made of materials used in the art, such as plastics and/or metals.

An ankle prosthesis may further comprise an actuator that drives the motion of the polycentric mechanism, and therefore drives the motion of the prosthesis, for instance as the prosthesis moves from heel strike to toe off. The actuator may be a linear actuator. The actuator may drive the motion of the polycentric mechanism by adjusting the distance between one point of the driven member and one point of the reference member. For example, the linear actuation system may adjust the distance between one point of the driven member, such as a hinge of the driven member, and one point of the reference member.

An ankle prosthesis embodiment may further exploit the kinematic property of the polycentric mechanism, such as the progression of the ICR position, and the position of the driven member's hinges in order to realize a fully powered motion of the ankle articulation. In various embodiments, the prosthesis may be sized as to support the ground reaction force ("GRF") profile over gait-time, which is elicited from the floor as the user walks, together with the angular range of motion of the ankle joint.

In certain embodiments, the linkages in the polycentric mechanism may be proportioned in order to provide the mechanism with an angular range of motion that mimics the angular range of motion of a natural, human ankle. For example, for an ankle prosthesis, an ankle range of motion for minimal mobility covers from 15° in plantar-flexion to 10° in dorsi-flexion. (Plantar-flexion is the position of a foot with the toe pointed downwards. Dorsi-flexion is the position of the foot with the toes pulled up towards the shin.) In various embodiments described herein, the ankle range of motion covers from at least 29° in plantar-flexion to at least 27° in dorsi-flexion. Additionally, certain linkages may be proportioned in order to provide a prospected displacement of the instantaneous center of rotation ("ICR"). For instance, the prospected displacement of the ICR becomes more advanced as the power requirements become higher. Placement of a linear actuator motorized axis can achieve a long enough lever-arm with respect to the ICR, so as to exert the torque that would otherwise be provided by a natural ankle. Identifying a proper mounting angle of the foot component and/or of the shank component with respect to the driven member and reference member respectively, can help center the polycentric mechanism's range of motion and the ICR trajectory in an appropriate position for covering anatomical gait requirements. For example, the mounting angle may be 19.5°.

FIGS. 1A-1D display side views of an embodiment of an ankle prosthesis at positions ranging from 0% of stride to 60% of stride. Each position is accompanied by three images in the figures. The left-hand image is a side view of an embodiment of a powered ankle-foot prosthesis, in a reference frame in which the foot is fixed, and in a posture corresponding to the stride percentage. The middle image is a side view kinematic representation of the same posture, with the GRF and active force represented in arrows. The GRF is represented in each image by the arrow that starts at the sole of the foot. In an embodiment, values associated with the GRF may be taken from information that is well known and documented in the art, and which, for instance, has been collected from studies involving GRF on human feet and ankles. Such values include the amount of the GRF, its orientation, and the position of the center of pressure (in other words, the position at the sole of the foot where the gray arrow originates).

The active force that the actuator is required to provide is represented in each image by the gray arrow that initiates at a point in the middle of the foot. Each middle image also traces a monocentric joint case, for comparison between the ICR position and the fixed joint. The position of the ICR is determined by the intersection of two lines, each congruent to each of the opposite sides of the quadrilateral figure of the reference member. The line segments resulting in the intersection are displayed as dashed lines.

Each right-hand image shows the same image as in the middle panel, but represented in a reference frame oriented according to the floor (x-axis is horizontal and y-axis is vertical), so that the transition of the prosthesis from 0% of stride to 60% of stride can be seen. Labels along x and y are distances in mm with respect to the heel location. Forces vector are scaled.

Figure 1C:
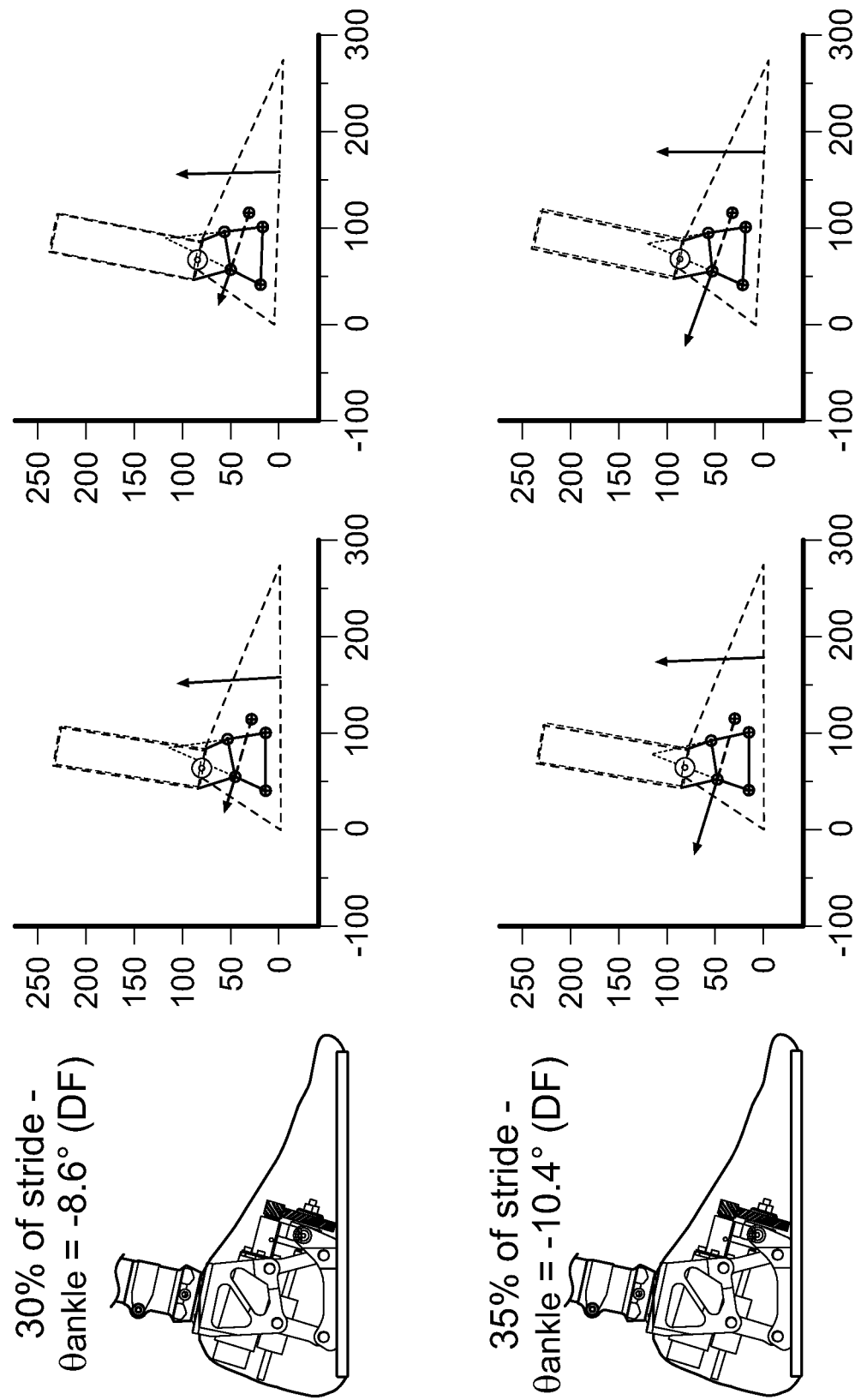
Figure 1C:
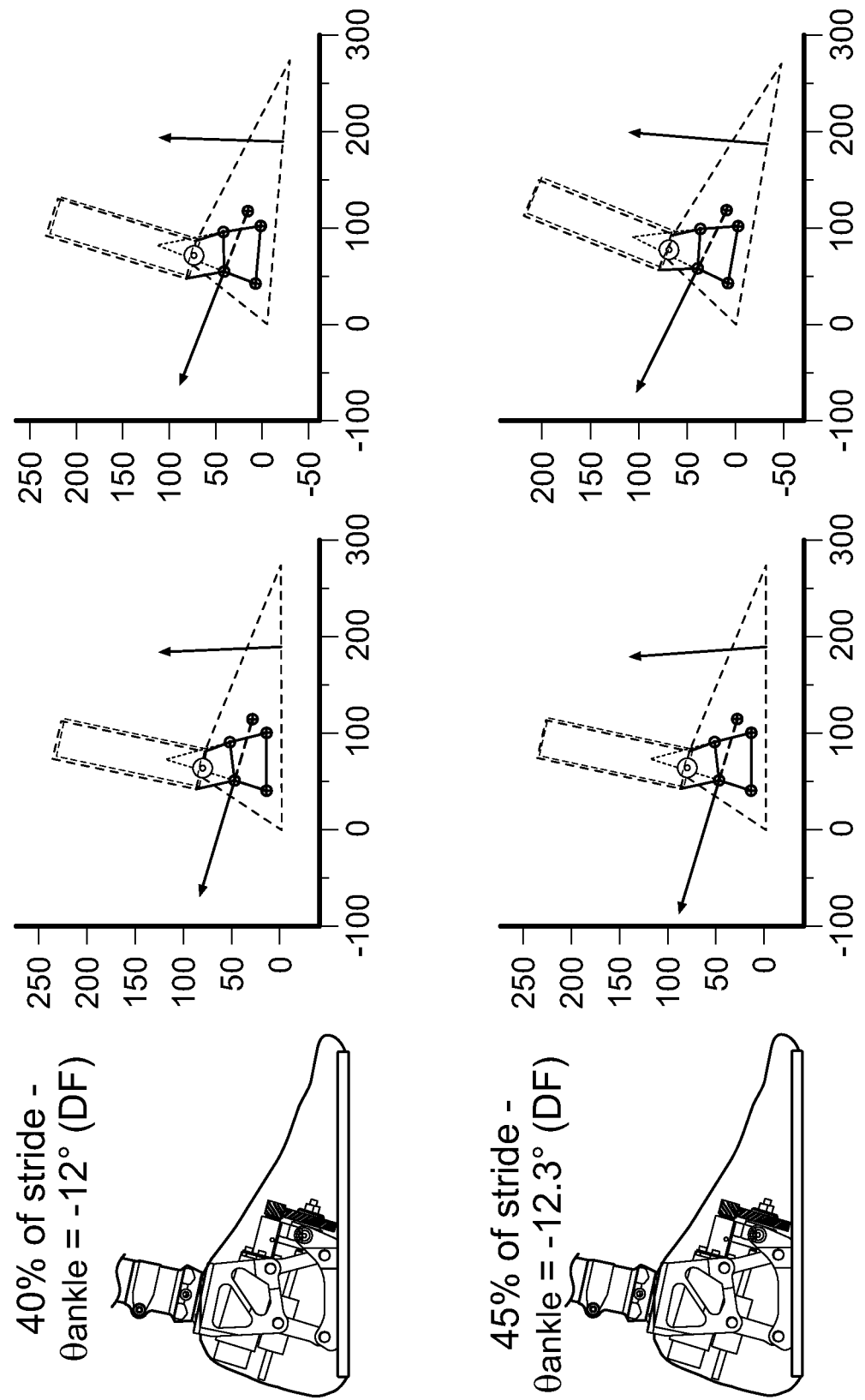
Figure 1D:
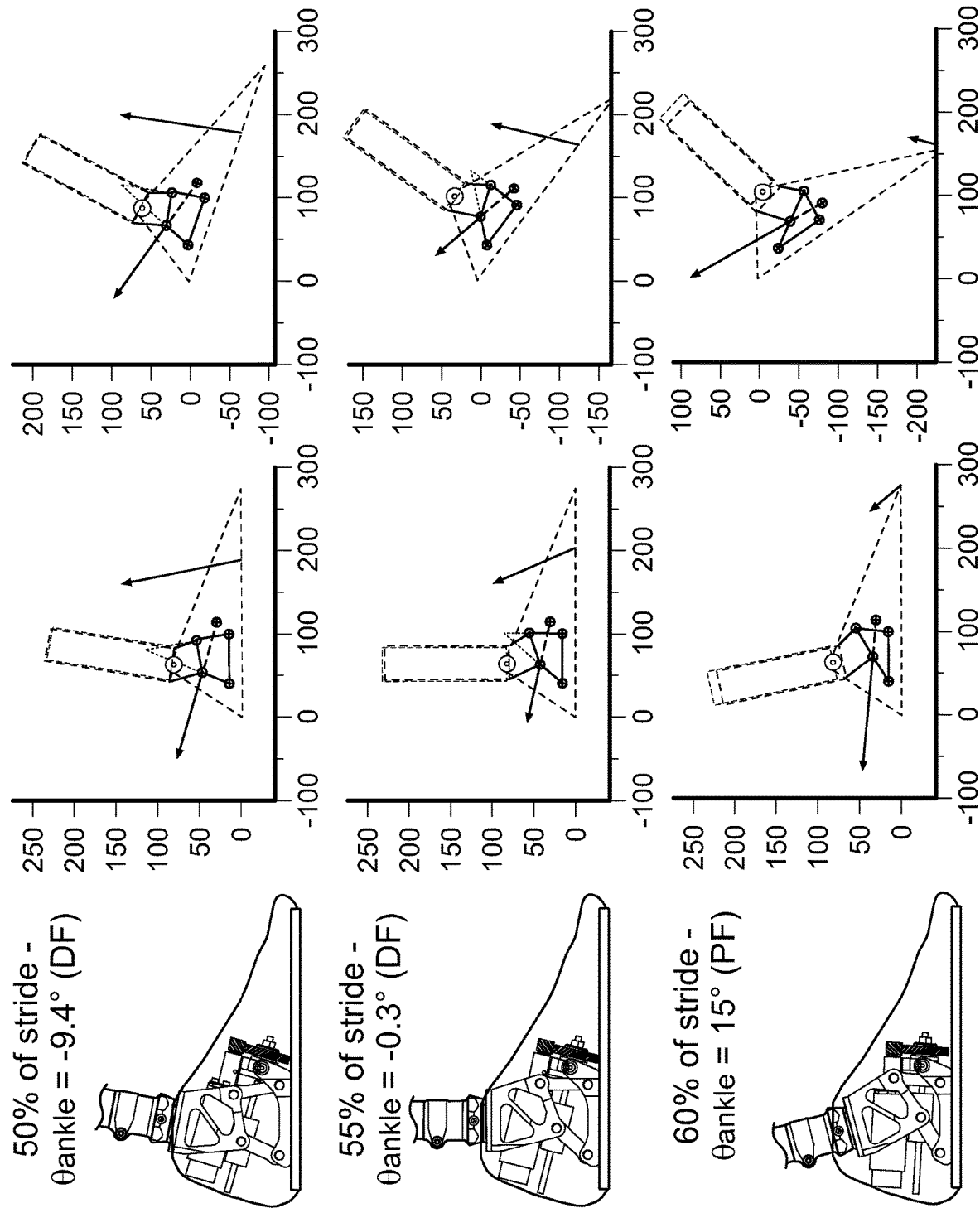

Briefly, the progression of the GRF with respect to the foot-ankle system during the stance phase of walking is depicted in FIGS. 1A-1D. For comparison, the middle images in each of FIGS. 1A-1D depict both the ICR and the monocentric center of rotation. The monocentric center of rotation is indicated in each figure as a circle with dot at its center, placed in between the foot component and the shank component. As the user walks, the center of pressure of recorded GRF from sound limb data progresses from the heel to the toe. In order to elicit the GRF being placed in a certain position under the foot, the ankle is expected to provide a certain torque. During gait, the most demanding phase for the ankle is in late stance, particularly during push off. During this period, the center of rotation is at a greater distance from the ankle, and the horizontal and total GRF are each greater than at other phases of stance. By moving the ICR outside the profile of the polycentric mechanism, the ICR is placed in an advantageous position during late stance, resulting in the GRF having a smaller lever arm than it would in a mono-centric system. For example, when the ankle is at about 45% of stride, as shown in FIG. 1C, the moment arm of the GRF to the monocentric center of rotation is substantially longer than the shortened moment arm of the GRF to the ICR. As a result, the amount of torque the GRF provides is lower, which means that the actuator may provide a lower amount of torque than it would need to in other systems, such as a mono-centric system. Other moment arms also are involved in the torque profile of the ankle prosthesis, as shown in the figures.

In the embodiment shown in FIGS. 1A-1D, the ICR trajectory is outside the profile of the polycentric mechanism, while the profile of the polycentric mechanism remains confined within the foot profile. Keeping the profile of the polycentric mechanism in the foot profile means that the artificial prosthesis has an aesthetically acceptable shape. It can, for instance, be inserted into an ordinary shoe, or otherwise sized so that it is not apparent to a casual observer that a person is using an artificial ankle or ankle-foot prosthesis.

Additionally, during an initial phase of stance, the actuator can function as a "brake" rather than an actuator, since the direction of active force and related equivalent ankle torque are opposite to the direction of the motion progression. In an embodiment, rather than the battery exerting energy during this phase, the actuator provides energy back to the battery, as the "braking" effect is given by the weight-acceptance back-driving the motor. For instance, if a backdrivable roller screw is used in the actuator, the "braking" effect may return energy to the battery. Backdrivable rollers screws are known in the art.

In a four bar polycentric mechanism, forces exchanged in between the driven and the fixed members, due to the polycentric mechanism connections, can arise but are geometrically aligned along the connecting cranks (being those connected through pivoting joints, they can only be compressed or tensed along their direction). Thus, whichever these components, they have a geometrically-null-arm with respect to the ICR (their direction are always crossing in the ICR): as a consequence, they do not change the exposed relationship between the actuated powered force and the GRF.

The actuator may comprise a rotating electrical motor, which is coupled to a linear screw-nut system. The actuator may convert rotating motion to linear motion, and vice versa. In another embodiment, a roller screw and a roller nut may be employed. The actuator may comprise a parallel-axis transmission stage, such as a pulley/belt system, or a geared system. The polycentric mechanism may provide for an opening in its interior, as shown in the various figures, such as an open space between the driven member's brackets where a portion of the actuator can be housed. This helps provide some degree of protection for the motor and any wiring of the actuator. As shown in the figures, the actuator can be enclosed in the foot shape, which can provide a substantial benefit to patients. In an embodiment, the actuator is so enclosed is as a result of placement of the actuator's axis, and the angled shape of the bracket 102 of the polycentric chain.

Figure 2A:
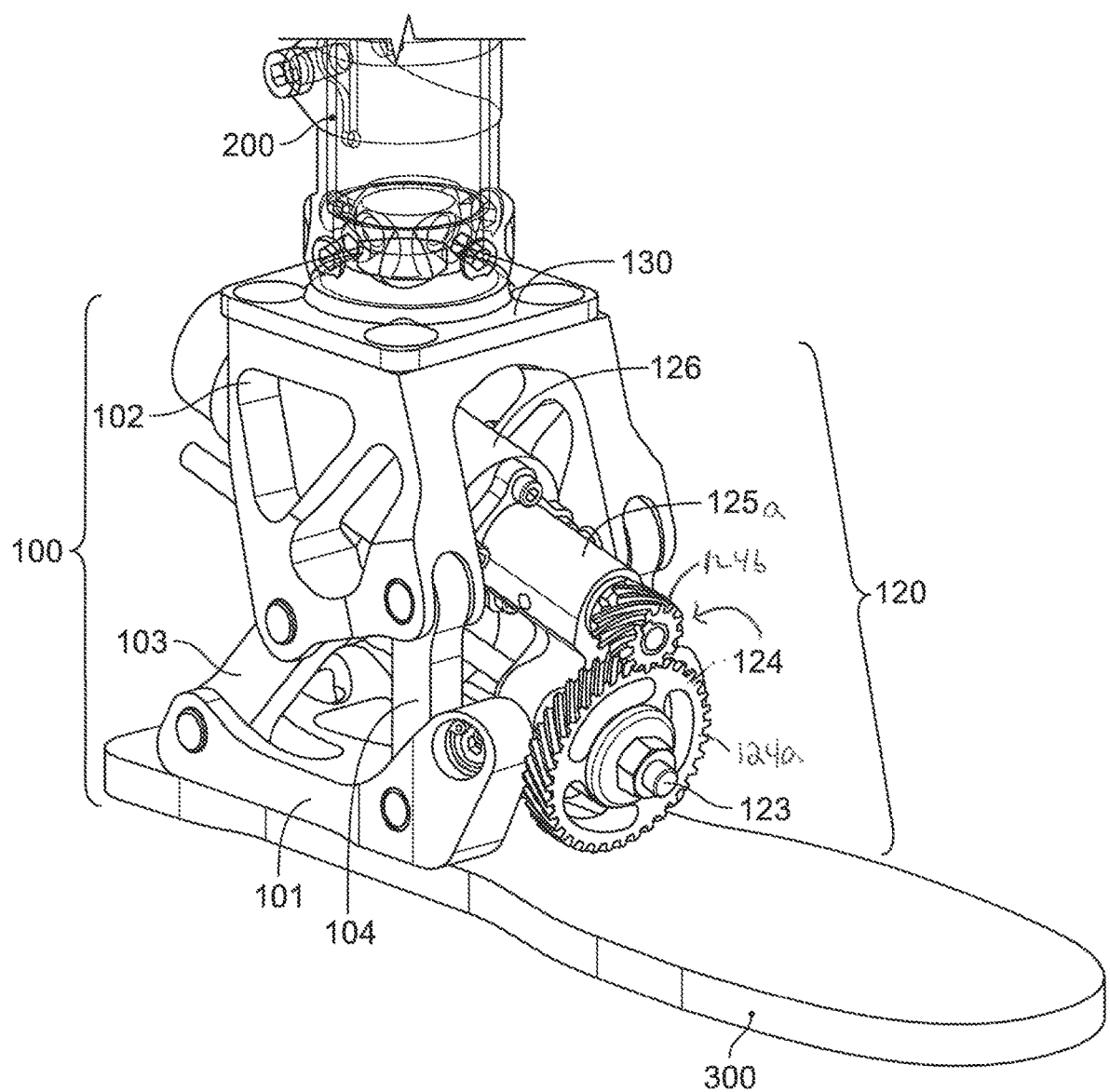
FIG. 2A displays a front three-quarter view of an embodiment of an ankle prosthesis.
Figure 2B:
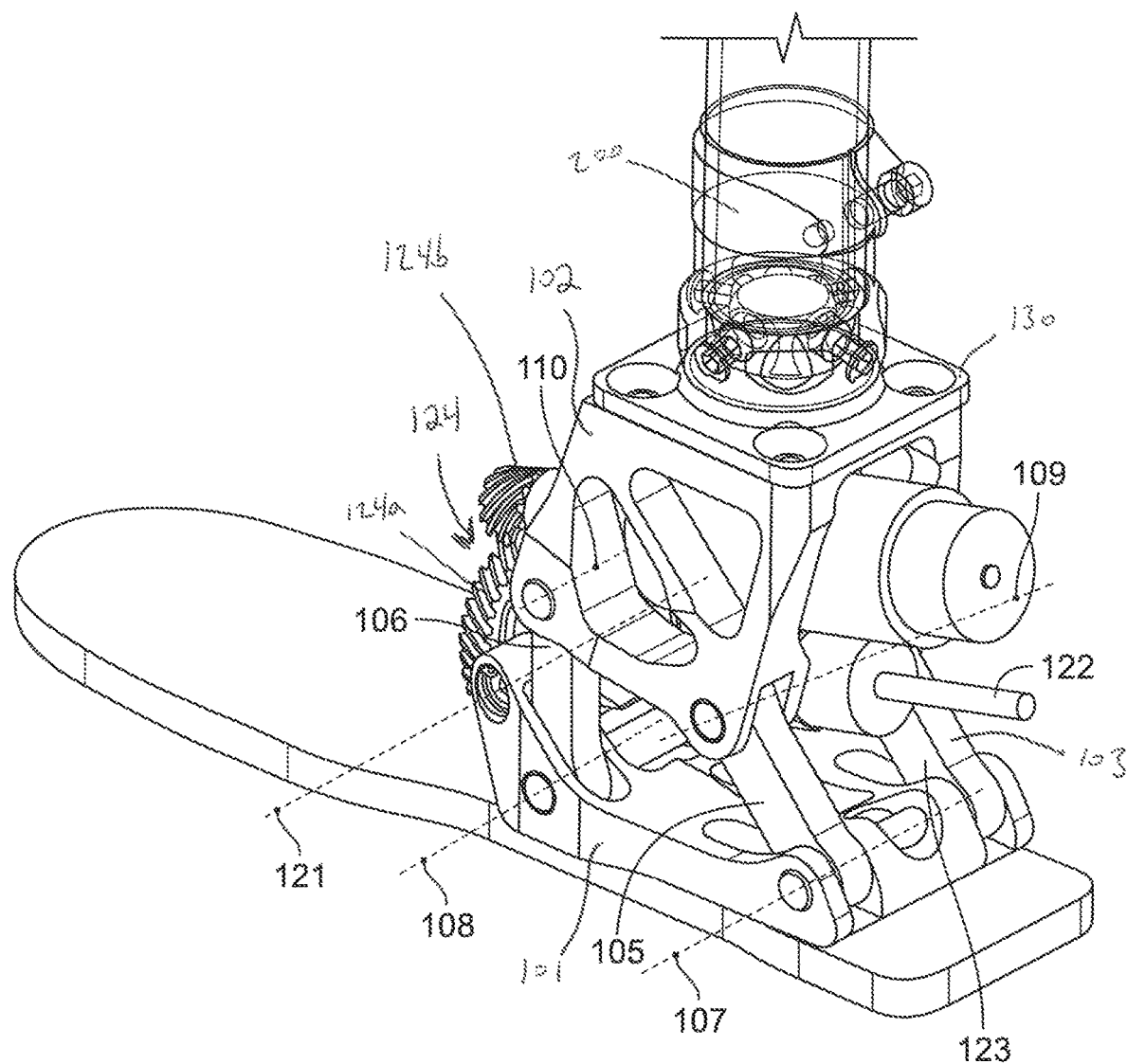
FIG. 2B displays a rear three-quarter view of an embodiment of an ankle prosthesis.

Description of the device mainly lies into the sagittal plane, while for the dimensions outside such plane, it can be seen from FIGS. 2A-2B how this is limited up to the size of a commercial pyramid connector 130, thus being competitive with all other foot and/or ankle prosthetic component of such genre. One embodiment of the assistive device is shown in FIG. 2. The assistive device 100 interfaces with a shank-pylon (or other prosthetic components) 200, via a modular connector 130, and with a foot 300 via direct fastening under the element 101.

The device 100 realizes the motion of the pylon 200 with respect to the foot 300 without co-locating the ankle joint in any physical position, but utilizing an exemplary polycentric mechanism with a resulting swiveling motion of the member 102 with respect to the member 101 on the lateral side of the device 100 and a resulting swiveling motion of the member 110 with respect to the member 101 on the medial side of the device 100. A kinematic chain is realized by connecting the two said members on each of the lateral or medial sides, via crank elements through four total pivoting axes (107-110). In particular, said cranks are replicated in pairs (103/105 and 104/106), connecting member 101 and member 102 both on the medial and on the lateral sides. As shown in FIG. 2A-2B, member 101 is connected to crank 103 and crank 105 via pins along the pivoting axis 107, and to cranks 104 and 106 via pins along the pivoting axis 108; member 102 is connected to crank 103 and crank 105 along the pivoting axis 109, and to crank 104 and crank 106 along the pivoting axis 110. Thus the same structure is provided on the medial and lateral sides of the device 100.

The device also includes an actuator, which may be housed within the opening between the two four-bar kinematic chain instances. The actuator provides power to assist motion of the device. In particular, the actuator exerts the required torque for the ankle flexion-extension movement. The actuator can adjust the distance between certain preferential axis pairs, such as the axis 109 and an additional axis 121 located in the foot component 101 as shown in FIG. 2B. Actuation can be realized via a linear element, such as a linear guide, a screw or a rail, and a sliding element such as a linear bushing, a nut or a carrier. The actuator may be attached to the two four-bar kinematic chain structures so that actuation of the actuator results in movement of one of the four-bar kinematic chain structures with respect to the other. As a result, relative position of the slider with respect to the guide can determine the posture of the four-bar kinematics. The actuator may be coupled to the polycentric mechanism in various ways, for instance as shown in the figures.

Figure 3A:
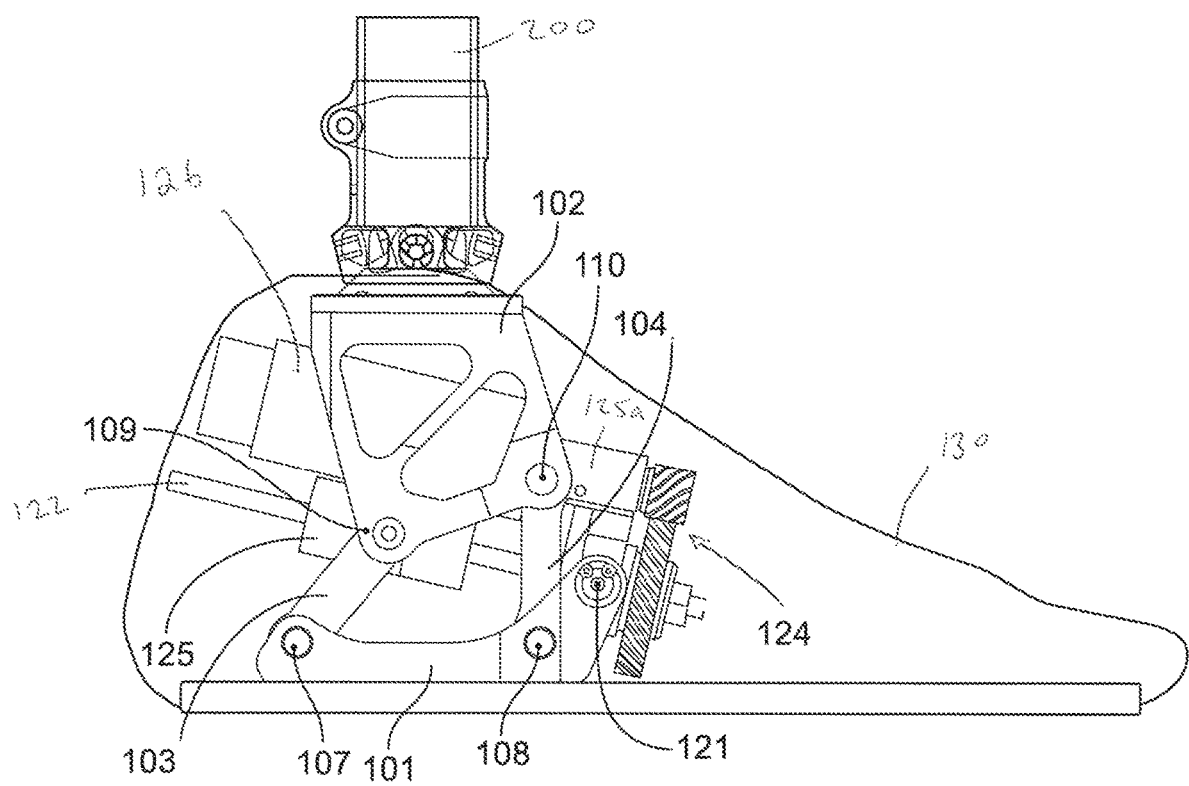
FIG. 3A displays a side view of an embodiment of an ankle prosthesis.

In one embodiment, shown in FIGS. 2A, 2B, and 3, the actuator 120 is powered with a rotational motor 126. The motor 126 may be, for example, a DC brushed or brushless electrical motor. The power of the motor 126 is transformed into linear motion by the screw/nut pair 122/125. In this embodiment, the nut 125 is connected to the element 102 and the cranks 103 and 105 via pins along the line of axis 109. The actuator may be interior to the element 102 as shown in FIGS. 2A and 2B. A transmission 124 comprising gears 124a and 124b transmits power from the motor 126 to the linear drive comprised by the screw 122 and the nut 125. A pivot element 125a (see FIG. 2A) may extend from the end of the motor 126 to a connection point to element 101 via a connector along the axis 121. Allowing the actuator 120 to pivot relative to the element 101 affixed to the foot 300 allows the actuator 120 to slightly rotate around axis 121 during gait. The slight rotation of the actuator 120 is reflected in the series of figures shown in FIG. 1A-1D.

It should be understood that other transmissions may be employed, such as a pulley-and-belt system or a different gearing system. The actuator 120 may employ other components known in the art of powered prostheses, such as control boards, motor controllers, microprocessors, memory, and so forth. The device 100 may provide ankle stiffness (such as physiological ankle stiffness) through, for example, software motor control. As shown by foot outline 120 in FIG. 3A, the device 100 can be fit within the profile of a human foot.

Figure 3B:
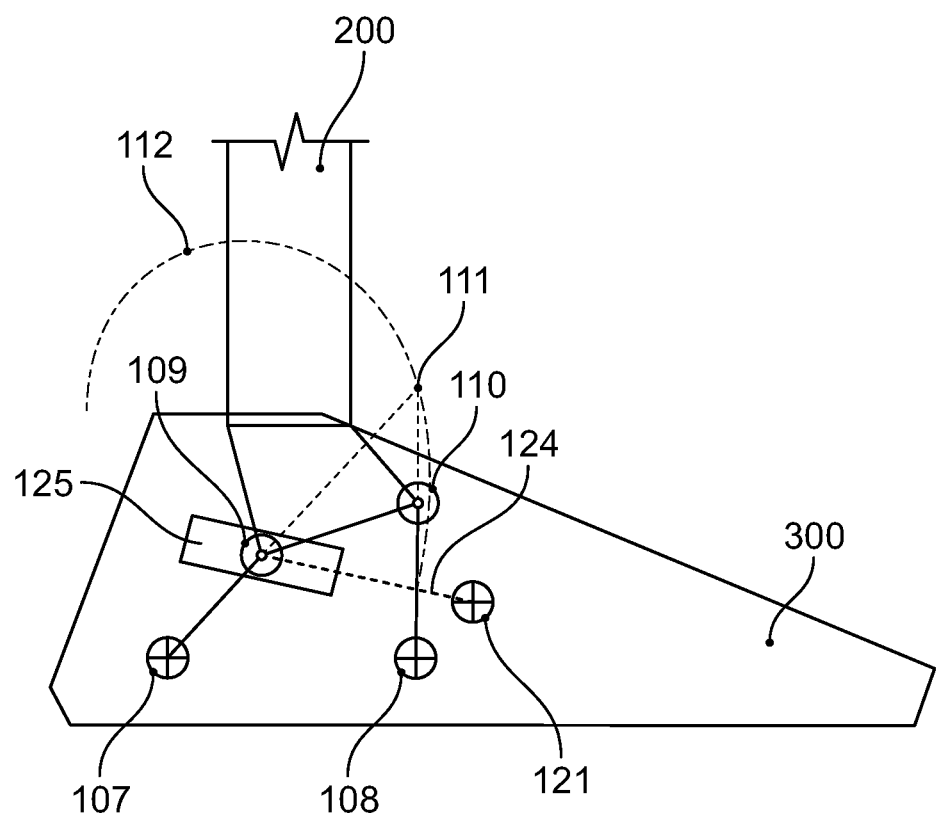
FIG. 3B displays a kinematic representation of an embodiment of an ankle prosthesis.

The device 100 can realize the ankle motion without constraining its mechanical components on a fixed hinge joint collocated on the ankle anatomical position itself, thus providing greater design freedom in mechanical and structural optimization. In particular, movement of the device 100 results in a motion between the foot component 300 and the shank component 200 which is substantially and aesthetically equivalent to a rotation around a fixed joint, but different in kinematics, shown in FIG. 3B. Instantaneously, the motion of the shank 200 with respect to the foot 300 corresponds to a rotation around the ICR 111, which (as discussed above) is not fixed. The arc 112 in FIG. 3B represents the trace of the ICR points as the device 100 from heel strike to toe off. The combination of rotation around the ICR, and the progression of the position of the ICR itself due to the polycentric mechanism's orientation, results in the global motion of the shank 200 with respect to the foot 300. In particular, the kinematic and kinetic characteristics (specifically, the angular range of motion and the transmission ratio from the actuator to the powered assistive torque) of the polycentric motion are completely defined by the arc 112 and ICR position 111. The assistive device 100 can provide the correct amount of powered torque for each angular position, properly evaluated accordingly to the kinematic of the ICR 111.

Simultaneously, the aesthetic appearance of the motion is also dependent on the relative position between the shank component 200 and the element 102. In one embodiment, shown in FIGS. 2-3, such relative position is optimized as to minimize the translational component of the swiveling motion parallel to the pylon axis itself (i.e. elevation or depression of the shank component 200 during motion).

In particular, being the physical motion of the shank component 200 depending also on the relative mounting between its interface and the member 102, this provides additional design parameters which can be conveniently tuned in order to meet particular characteristics in the motion, e.g. having a bigger foot clearance during swing phase.

Figure 4A:
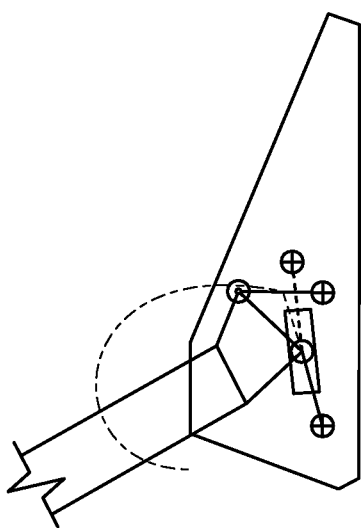
FIG. 4A displays a side view of a plantar-flexed ankle prosthesis embodiment and a kinematic representation of a plantar-flexed ankle prosthesis embodiment, in either stance or swing phase.
Figure 4A:
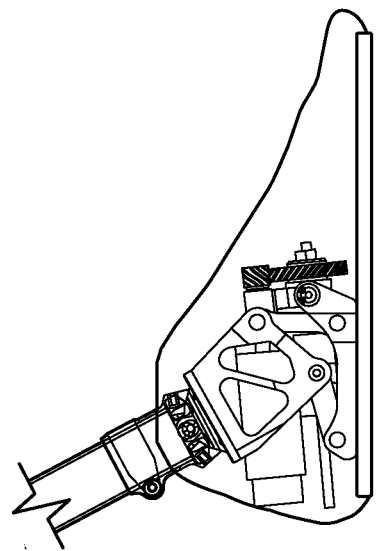
Figure 4B:
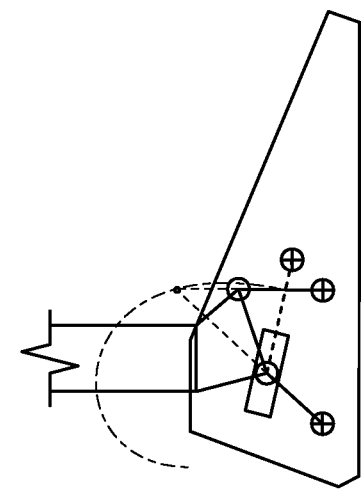
FIG. 4B displays a side view of a neutral ankle prosthesis embodiment and a kinematic representation of a neutral ankle prosthesis embodiment, in either stance or swing phase.
Figure 4B:
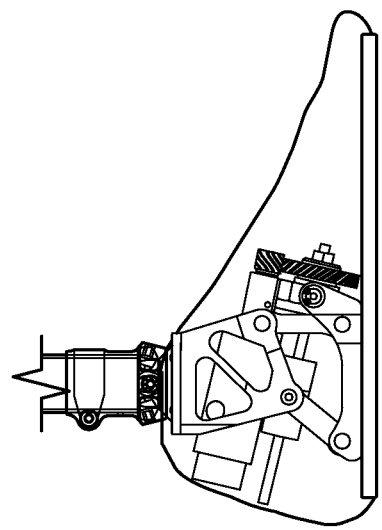
Figure 4C:
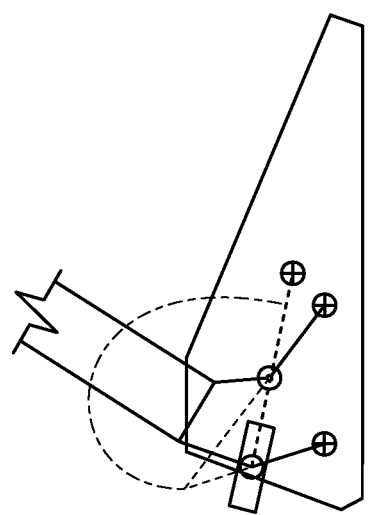
FIG. 4C displays a side view of a dorsi-flexed ankle prosthesis embodiment and a kinematic representation of a plantar-flexed ankle prosthesis embodiment, in either stance or swing phase.
Figure 4C:
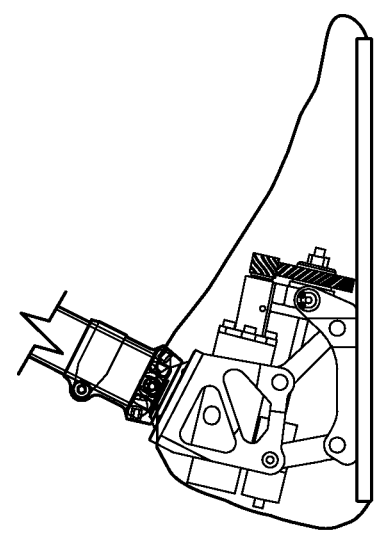
Figure 5:
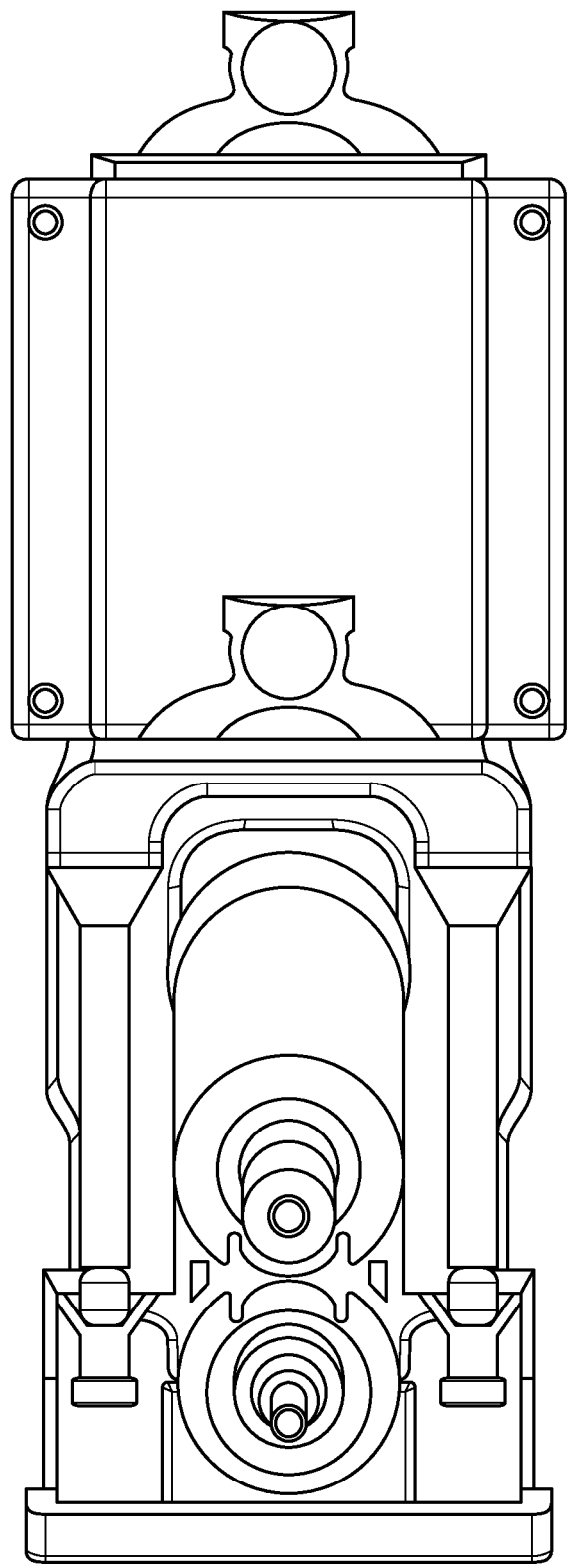
FIG. 5 displays a rear view of a prosthesis embodiment.
Figure 6:
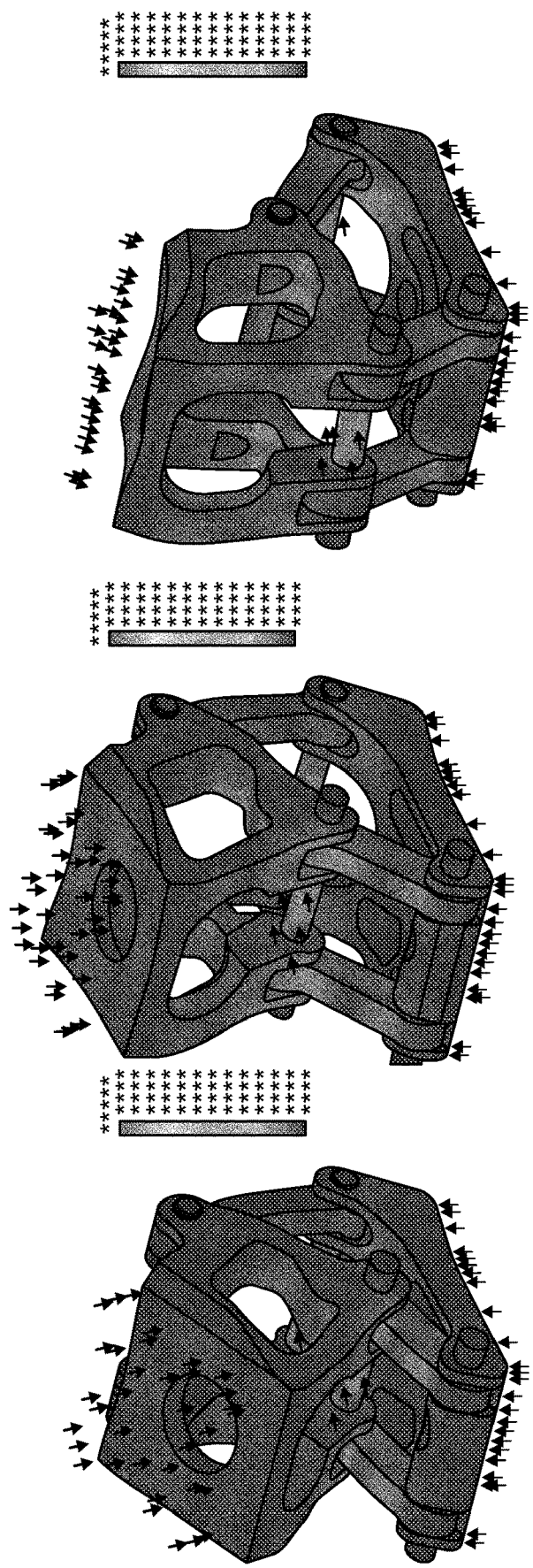
FIG. 6 displays various views of structural analysis of an embodiment.

Behavior of the represented embodiment with the extremal device postures (maximum plantar-flexion and dorsi-flexion), together with the neutral one, is shown in FIGS. 4A-4C. In particular, the greater deviation of the trace 112 from a closed point (ideal condition for a polycentric motion perfectly corresponding to a fixed-hinged rotation) occurring in high values of the plantar-flexion, which are commonly not exploited during the level walking gait. Plantar-flexed, neutral and dorsi-flexed position of the prosthesis and corresponding kinematic scheme, with position of ICR for current configuration. The range of motion covers about 30° in both plantar-flexion (FIG. 4A) and dorsi-flexion (FIG. 4C).

The embodiments described herein are intended to be merely exemplary, and numerous variations and modifications will be apparent to those skilled in the art. All such variations and modifications are intended to be within the scope of the present invention as defined in the appended claims.

What is claimed is:
1. A powered ankle prosthesis, comprising
a shank component and a foot component;
a polycentric mechanism having a profile and a defined path for an instantaneous center of rotation, a first linkage to enable movement of the shank component with respect to the foot component, and a second linkage for providing power to the first linkage;

the first linkage comprises a driven member coupled to the shank component, a reference member coupled to the foot component, and a plurality of cranks pivotably connected to the driven member and to the reference member;

the second linkage providing power to the driven member of the first linkage, resulting in a swiveling motion between the reference member and the driven member;

the second linkage comprises a motor for generating power to operate the prosthesis, a transmission and a linear actuator, the transmission transmitting power from the motor to the linear actuator, the linear actuator imparting linear motion to the driven member, thereby causing the driven member and the plurality of cranks to move relative to the reference member;

wherein the path of the instantaneous center of rotation is defined by a trajectory substantially equal to an arc positioned over a joint of the polycentric mechanism, and wherein the instantaneous center of rotation is located outside of the profile of the polycentric mechanism and anterior of the ankle prosthesis in a stance phase of gait where the ankle angle ranges from approximately 15° and −12°.

2. The prosthesis of claim 1, wherein the path of the instantaneous center of rotation is further defined such that during late stance, the instantaneous center of rotation is positioned to provide a shortened moment arm in relation to a ground reaction force.

3. The prosthesis of claim 2, wherein the reference member defines the path for the instantaneous center of rotation.

4. The prosthesis of claim 3,
a. wherein the reference member comprises a base element connected to a foot component, the plurality of cranks comprising a first crank and a second crank, the first crank pivotally coupled to the reference member, and the second crank pivotally coupled to the reference member;
b. wherein the first crank and the second crank each are pivotally coupled to a bottom portion of the driven member; and
c. wherein the first crank and the second crank are aligned to define the path for the instantaneous center of rotation.

5. The prosthesis of claim 4, wherein a top portion of the driven member is angled for attachment to the shank component.

6. The prosthesis of claim 2, the linear actuator exerts a required amount of torque for flexion-extension movement of the prosthesis.

7. The prosthesis of claim 6, wherein the linear actuator is at least partially housed within an opening of the polycentric mechanism.

8. The prosthesis of claim 7, wherein the linear actuator is configured to adjust the distance between a hinge of the reference member and a hinge of the driven member.

9. The prosthesis of claim 1, wherein the polycentric mechanism fits within the contour of an anatomical foot profile.

10. The prosthesis of claim 1, wherein the second linkage is at least partially housed within an opening of the driven member and pivotably mounted to the reference member.

11. A powered ankle prosthesis, comprising:
a polycentric mechanism having a defined path for an instantaneous center of rotation; wherein the path of the instantaneous center of rotation is defined by a trajectory substantially equal to an arc positioned over a joint of the polycentric mechanism; and
an actuator for moving the polycentric mechanism, the actuator comprising a motor, a transmission, and a screw, wherein the actuator is at least partially housed within an opening of the polycentric mechanism and configured to adjust the distance between a hinge of a first member and a hinge of a second member.

12. The prosthesis of claim 11, wherein the screw is a lead-screw.

13. The prosthesis of claim 11, wherein the screw is a ball-screw.

14. The prosthesis of claim 11, wherein the screw is a roller-screw.

15. A powered ankle prosthesis, comprising
a shank component and a foot component;
a polycentric mechanism having a profile and a defined path for an instantaneous center of rotation; a first linkage to enable movement of the shank component with respect to the foot component, and a second linkage for providing power to the first linkage;
the first linkage comprises a driven member coupled to the shank component, a reference member coupled to the foot component, and a plurality of cranks pivotably connected to the driven member and to the reference member;
the second linkage providing power to the driven member of the first linkage, resulting in a swiveling motion between the reference member and the driven member;
the second linkage comprises a motor for generating power to operate the prosthesis, a transmission and a linear actuator, the transmission transmitting power from the motor to the linear actuator, the linear actuator imparting linear motion to the driven member, thereby causing the driven member and the plurality of cranks to move relative to the reference member;
the linear actuator operatively coupled to the polycentric mechanism for exerting torque required for flexion-extension movement of the ankle prosthesis;
wherein the path of the instantaneous center of rotation is defined by a trajectory substantially equal to an arc positioned over a joint of the polycentric mechanism, and wherein the instantaneous center of rotation is located outside of the profile of the polycentric mechanism and anterior of the ankle prosthesis when the ankle prosthesis is in a neutral position associated with standing.

\* \* \* \* \*